United States Patent
Radcliffe et al.

(10) Patent No.: US 9,055,983 B1
(45) Date of Patent: Jun. 16, 2015

(54) SELF-LOCKING BONE SCREW RECEIVER

(71) Applicants: Jeffrey Scott Radcliffe, Marietta, GA (US); Michael Glatzer, Alpharetta, GA (US); Mark Wilson Jacob, Acworth, GA (US); Reginald Antonio Terrell, Marietta, GA (US)

(72) Inventors: Jeffrey Scott Radcliffe, Marietta, GA (US); Michael Glatzer, Alpharetta, GA (US); Mark Wilson Jacob, Acworth, GA (US); Reginald Antonio Terrell, Marietta, GA (US)

(73) Assignee: Amendia, Inc., Marietta, GA (US)

( * ) Notice: Subject to any disclaimer, the term of this patent is extended or adjusted under 35 U.S.C. 154(b) by 14 days.

(21) Appl. No.: 14/260,361

(22) Filed: Apr. 24, 2014

(51) Int. Cl.
*A61B 17/80* (2006.01)
*A61B 17/86* (2006.01)

(52) U.S. Cl.
CPC ..... *A61B 17/8042* (2013.01); *A61B 2017/8655* (2013.01); *A61B 17/8033* (2013.01); *A61B 17/8047* (2013.01)

(58) Field of Classification Search
CPC ........... A61B 17/8042; A61B 17/8052; A61B 17/7058; A61B 17/8033; A61B 17/86; A61B 17/8038; A61B 17/8047; A61B 2017/8655; A61B 2017/867; A61B 2017/8695; F16B 41/00
USPC ......... 606/267–272, 289, 291, 293–295, 308; 411/999
See application file for complete search history.

(56) References Cited

U.S. PATENT DOCUMENTS

| | | | | |
|---|---|---|---|---|
| 3,525,108 A | * | 8/1970 | Holton | 470/2 |
| 4,329,097 A | | 5/1982 | Steele et al. | |
| 4,478,478 A | * | 10/1984 | Durand et al. | 439/723 |
| 4,640,524 A | * | 2/1987 | Sedlmair | 280/611 |
| 4,793,757 A | * | 12/1988 | Peterson | 411/533 |
| 4,865,335 A | * | 9/1989 | McGann | 277/606 |
| 5,082,407 A | * | 1/1992 | Mickiewicz | 411/107 |
| 5,544,902 A | * | 8/1996 | Belter | 277/630 |
| 5,709,686 A | * | 1/1998 | Talos et al. | 606/281 |
| 6,093,899 A | * | 7/2000 | Takano et al. | 200/302.1 |
| 6,258,089 B1 | | 7/2001 | Campbell et al. | |
| 6,331,179 B1 | * | 12/2001 | Freid et al. | 606/279 |
| 6,361,537 B1 | | 3/2002 | Anderson | |
| 6,371,492 B1 | * | 4/2002 | Baron | 277/637 |
| 6,602,255 B1 | | 8/2003 | Campbell et al. | |
| 7,182,782 B2 | * | 2/2007 | Kirschman | 623/17.11 |
| D603,962 S | * | 11/2009 | Kriska et al. | D24/155 |
| 7,662,174 B2 | | 2/2010 | Doubler et al. | |
| 7,766,948 B1 | * | 8/2010 | Leung | 606/305 |

(Continued)

*Primary Examiner* — Michael T Schaper
*Assistant Examiner* — Amy Sipp
(74) *Attorney, Agent, or Firm* — David L. King (57) ABSTRACT

The present invention provides a unique way to provide a self-locking screw opening that has no separate parts. The self-locking feature (20) is formed in the wall (11) of the screw receiver opening (12) and automatically locks a screw (100) from backing out. During insertion of the screw (100) into bone, the screw head (110) passes one or more, preferably two nubs (20) or one or more projections (20) formed into the surface wall (11) of the receiver opening (12), and as the screw (100) is threaded into the bone, the screw head (110) contacts the nubs (20) or projection (20) and the screw (100) is deflected slightly in a direction opposite the nubs (20) or projection (20) allowing the screw head (110) to pass by the nubs (20) or projection (20) locking the screw (100) from backing out.

14 Claims, 6 Drawing Sheets

(56) References Cited

U.S. PATENT DOCUMENTS

| | | |
|---|---|---|
| 8,043,346 B2 | 10/2011 | Markworth |
| RE43,008 E * | 12/2011 | Talaber et al. .................. 606/71 |
| 8,372,152 B2 * | 2/2013 | Kirschman ................ 623/17.16 |
| 8,425,607 B2 | 4/2013 | Waugh et al. |
| 8,454,666 B2 | 6/2013 | Tornier |
| 8,556,944 B2 * | 10/2013 | Dube et al. .................... 606/282 |
| 8,562,656 B2 * | 10/2013 | Humphreys .................. 606/289 |
| 8,616,818 B2 * | 12/2013 | Travis ........................... 411/533 |
| 8,852,249 B2 * | 10/2014 | Ahrens et al. ................. 606/291 |
| 8,858,603 B1 * | 10/2014 | Zufelt ........................... 606/289 |
| 2002/0173790 A1 * | 11/2002 | Chang et al. .................... 606/61 |
| 2005/0137597 A1 * | 6/2005 | Butler et al. .................... 606/69 |
| 2006/0009770 A1 * | 1/2006 | Speirs et al. .................... 606/69 |
| 2006/0195085 A1 * | 8/2006 | Happonen et al. ............... 606/61 |
| 2006/0195100 A1 * | 8/2006 | Kirschman ...................... 606/69 |
| 2008/0015592 A1 * | 1/2008 | Long et al. ....................... 606/69 |
| 2008/0234751 A1 * | 9/2008 | McClintock ................... 606/291 |
| 2009/0036933 A1 * | 2/2009 | Dube et al. ..................... 606/282 |
| 2011/0093016 A1 * | 4/2011 | Aferzon ......................... 606/279 |
| 2011/0106159 A1 * | 5/2011 | Nazeck .......................... 606/246 |
| 2012/0191141 A1 * | 7/2012 | Costabile ....................... 606/295 |
| 2012/0197307 A1 * | 8/2012 | Fritzinger et al. ............. 606/289 |
| 2012/0323281 A1 * | 12/2012 | Orbay et al. ................... 606/281 |
| 2013/0012993 A1 * | 1/2013 | Biyani et al. ................... 606/246 |
| 2013/0184767 A1 * | 7/2013 | Kaufman et al. ............... 606/290 |
| 2014/0172022 A1 * | 6/2014 | Suh ................................ 606/291 |
| 2014/0214092 A1 * | 7/2014 | Wolter ........................... 606/289 |
| 2014/0277175 A1 * | 9/2014 | Campbell et al. ............. 606/281 |

* cited by examiner

SELF-LOCKING BONE SCREW RECEIVER

TECHNICAL FIELD

The present invention is directed to a unique self-locking feature integral to a receiver opening for supporting a bone screw head, the self-locking feature prevents the screw from backing out of the receiver opening on insertion.

BACKGROUND OF THE INVENTION

The use of pedicle bone screws with an enlarged head supported in an opening of a receiver type device such as a plate, an implant or a tower or tulip type device is well known. The enlarged heads are typically supported in a complimentary seat at the base of the opening. During a surgical procedure, the screw is often held on assembly into a device. The pedicle or bone screw has threads adapted to engage bone. The bone can be pre-drilled or often the threads are of a self-tapping variety that drill themselves into the bone. Once fully threaded into the bone by a screw driver device, the screw ideally should not loosen. To insure this loosening does not occur, a variety of screw locking devices have been developed to prevent the screw from backing out of the bone and loosening. These added locking features are separate parts installed over the screw head typically, some are spring loaded devices that can deflect out of the path of the screw head on installation and snap over the screw head on tightening. The preferred locks are held in the device being anchored by the screw and automatically move into locking position so the surgeon does not need to do any additional steps to lock the screw in place.

These separate locking features add cost and complexity to the device being anchored. The need to avoid loosening bone screws, however, has justified this added burden.

SUMMARY OF THE INVENTION

The present invention provides a unique way to provide a self-locking screw opening that has no separate parts. The self-locking feature is formed in the wall surface of the screw receiver opening and automatically locks the screw from backing out. During insertion of the screw into bone, the screw head passes one or more, preferably two nubs or one or more projections formed into the surface wall of the receiver opening, and as the screw is threaded into the bone, the screw head contacts the nubs or projections and the screw is deflected slightly in a direction opposite the nubs or projections allowing the screw head to pass by the nubs or projections locking it from backing out. Preferably, the receiver opening has a seat in a base of the opening and the wall has a diameter closely sized to the screw head. In this construction, a recessed groove or channel is cut into the wall diametrically opposite the nub or projection to allow the deflected screw head to enter past the nub or projection into a seat of the receiver opening as it is being deflected by the nubs or projection. It is this accommodation that allows the screw to easily pass the nubs or projection at a controlled force or torque, typically less than 10 lbs or 10 in lb, ideally above 2 to 6 lbs force or in lb torque. The nubs or projections provide a noticeable resistance that is felt easily by the surgeon as the screw passes this locking feature assuring the surgeon the screw is locking in place.

The design is uniquely adapted to work with no changes to the screw head in terms of dimensions or tolerances and can work with a variety of screw head shapes such as monoaxial, dual axial, polyaxial, conical, hemispherical, flat head or the like. Typically, bone screws are sized in diameters of 1 mm to 6.5 mm or higher up to 7.5 mm or even 8 mm. The present invention can work with any size bone screw.

BRIEF DESCRIPTION OF THE DRAWINGS

The invention will be described by way of example and with reference to the accompanying drawings in which.

DETAILED DESCRIPTION OF THE INVENTION

Figure 4:
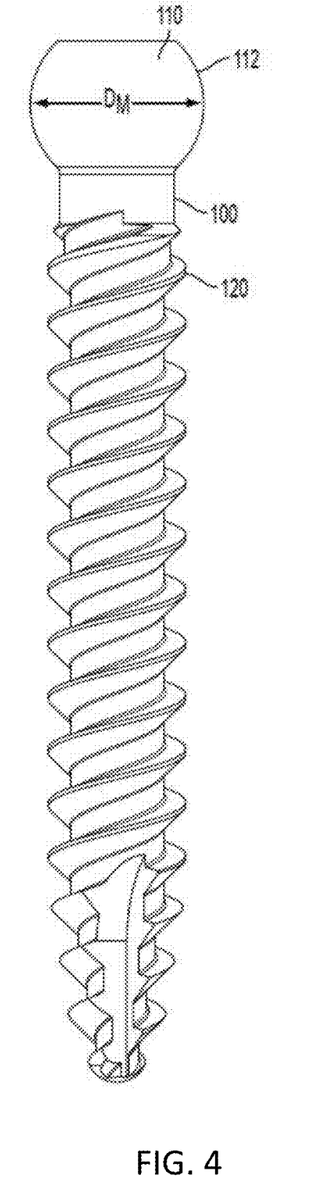
FIG. 4 is an exemplary bone screw shown in perspective view.

FIG. 4 is an exemplary typical pedicle bone screw 100. The screw 100 has a threaded shank 120 for threadingly engaging bone and an enlarged head. The head 110, as illustrated, has a central tool opening 111 to accept a screw driver device. The head 110 as illustrated has an enlarged bulbous portion, as shown; the head 110 has a spherical contour surface 112 that increases from the shank to a maximum diameter $D_M$ at about midway up the head and the curvature decreasing from maximum diameter $D_M$ to a flat top surface. As shown, the curvature surface 112 of the exemplary head 110 is uniform of a constant radius. It is understood the bone screw could employ any number of shapes, but the self-locking feature has to allow entry of the screw head 110 to slide or pass over the nubs or projections 20 at the maximum diameter $D_M$ location of the screw head 110.

When the screw 100 is inserted into the receiver device 10 at a receiving opening 12, the opening 12 will have a complimentary seat surface 14 to support and hold the lower surface of the screw head 110. The complimentary surface has a similar mating profile to the screw head 110 lower portion.

This, in some shapes such as the exemplary head 110, allows the screw 100 to pivot in any direction about the seat 14. This feature commonly is referred to as "polyaxial" and it allows the screw threaded shank to make an alignment adjustment to optimize the bone attachment location. The screw 100, as illustrated, has a self-tapping thread 120 shown in FIG. 4.

Figure 1:
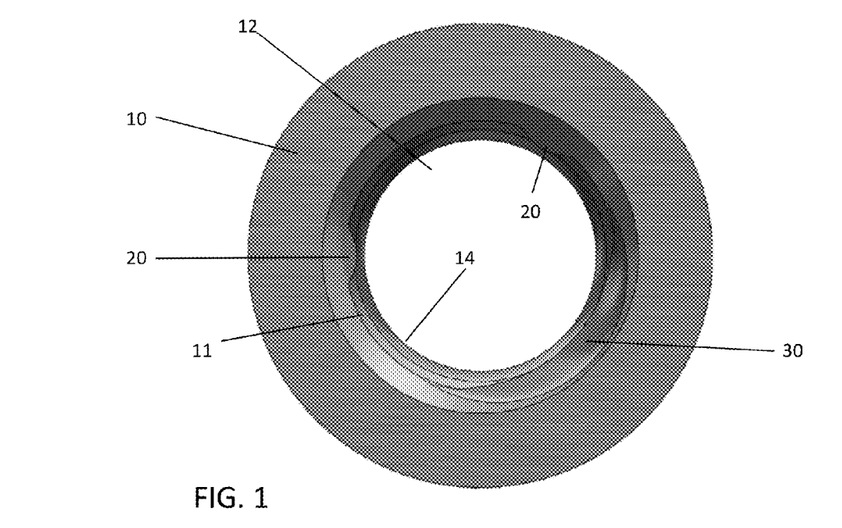
FIG. 1 is a top view of the self-locking feature of an exemplary receiving opening without a screw installed.
Figure 2:
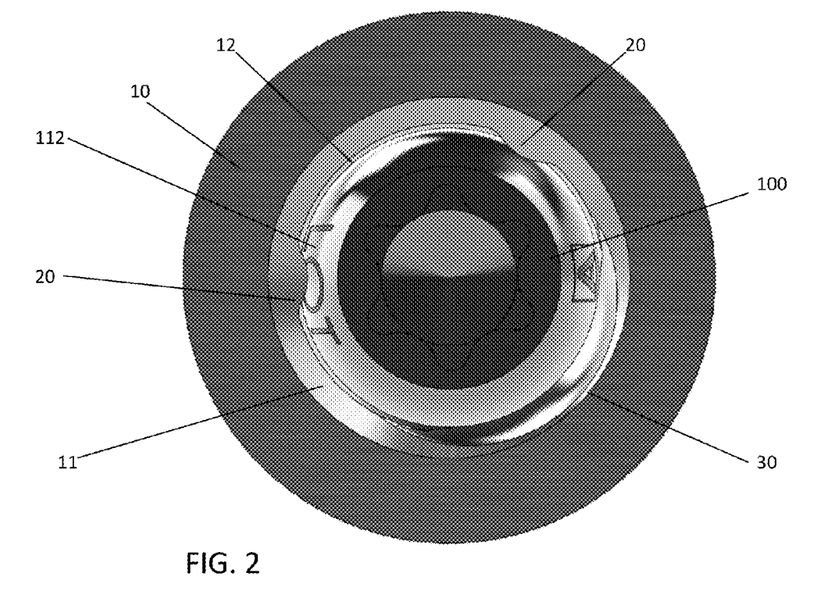
FIG. 2 is a top view of the exemplary receiving opening of FIG. 1 with a screw installed.
Figure 3A:
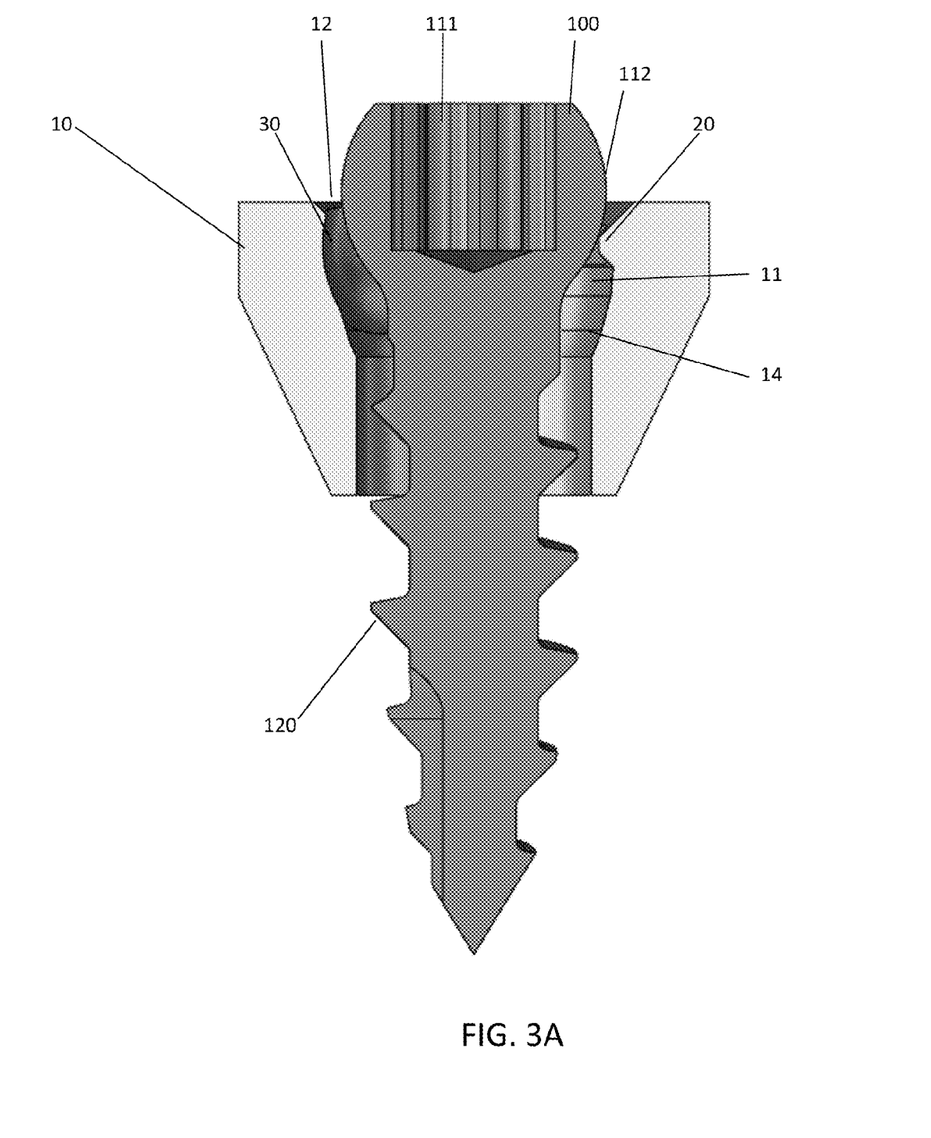
FIG. 3A is a cross sectional view of the screw initial contacting the self-locking feature.
Figure 3B:
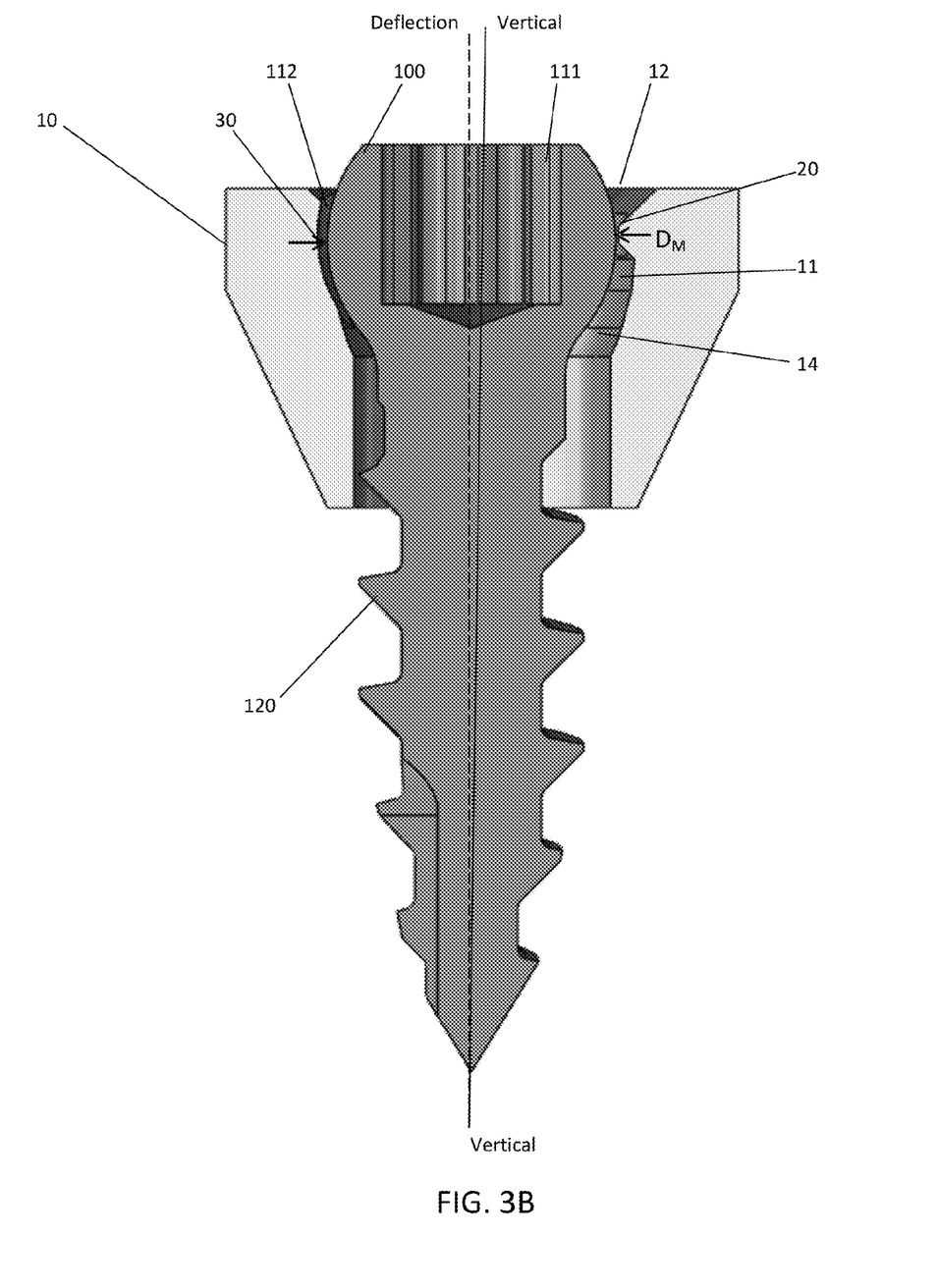
FIG. 3B is the screw deflected at the maximum diameter shown in cross section.
Figure 3C:
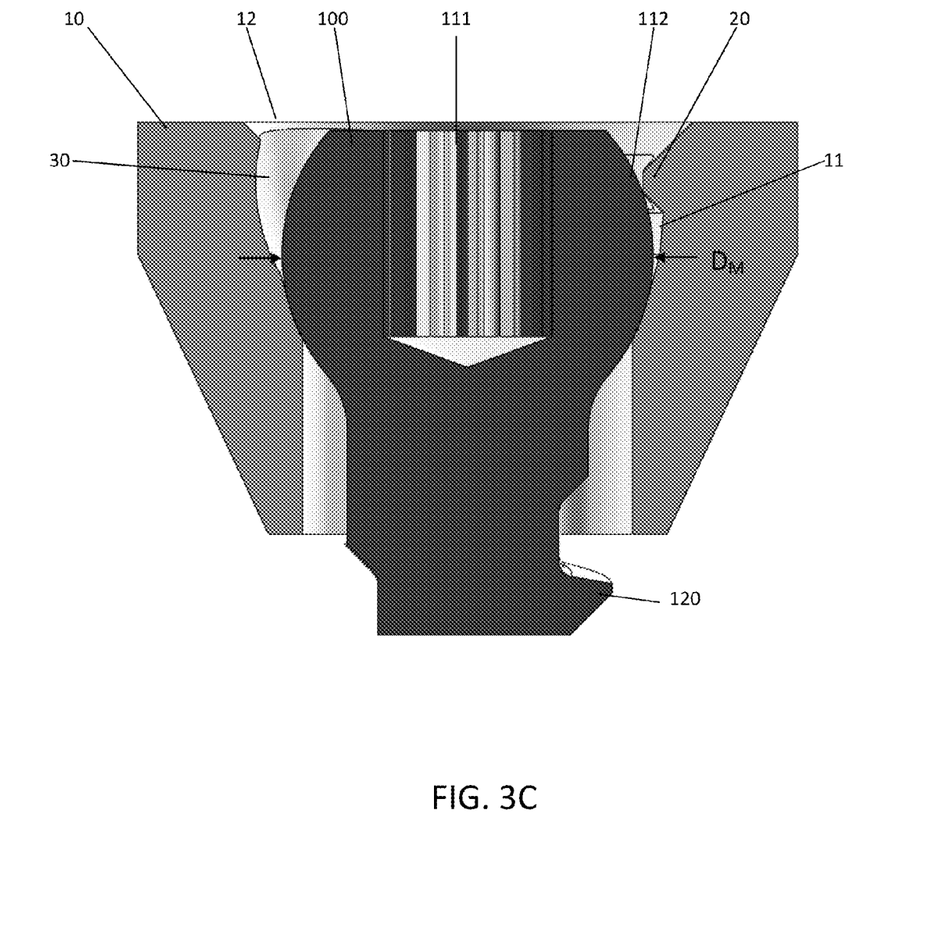
FIG. 3C is a cross sectional view of the installed screw and receiving opening of FIG. 2 taken along lines 3-3.

With reference to FIG. 1, a top view of a receiver 10 having an opening 12 is shown. The receiver 10 is an exemplary embodiment showing how an opening can be manufactured with the self-locking feature 20 provided within an opening 12 of the receiver 10. The self-locking feature 20, as illustrated in FIG. 2, is one or more nubs, as shown, two nubs 20 that project from the inner wall 11 of the opening 12. The projections or nubs 20 as shown are positioned on one side of the opening 12 at an angle relative to the other nub 20 at about 120 degrees relative to the axis of the opening 12. Directly opposing and opposite the nubs or projections 20 is a recessed groove 30 cut into the wall 11. As shown, the recessed groove 30 provides a depression or concavity in the wall 11 of a sufficient size to accommodate a screw head 110 that is deflected upon contact with the projections 20. It is important to note the projections 20 as shown while positioned at 120 degrees apart could be positioned at alternative angles however it is important that the projections 20 are provided in such a way that they diametrically are able to push the screw head 110 in a common direction. It is important that the screw head 110 deflects uniformly in a known direction. For example, if the projections 20 were positioned at 180 degrees apart, it is not clear which direction the screw head 110 would need to deflect as it tries to pass and in fact may not be able to pass efficiently. Accordingly, it is important to note, that providing additional projections 20 around the periphery limits the ability of the screw head 110 to actually deflect. For example, if three projections were provided, each at 120 degrees apart, then the screw head 110 would be symmetrically pushed and there would be no opportunity for the screw head 110 to deflect in one direction or another relative to the inner wall 11 of the opening 12. In such a fashion, the screw head 110 would then have to be pressed over the projections 20. This would limit the amount of locking force that could be provided because if the projections 20 were symmetrically oriented, the surgeon would have a difficult time driving the screw head 110 past the projections. By providing them such that they are an eccentric orientation on one half of the opening 12 such that they can directionally push the screw head 110 in a known direction allows for the surgeon to continue to drive the screw driver rotating the screw into the screw head 110 in such a fashion that as the screw 100 makes initial contact with the projections 20 as shown in FIG. 3A, the screw head 110 will then start to deflect. This deflection is minimal in that it occurs primarily at the top of the screw head 110 and even if the screw 100 is rigid, it only increases the load slightly on one side of the bone opening without damaging or stripping any threads formed in the bone. It just increases the pressure slightly along the side of deflection as the screw 100 is being continually driven. The projections 20 are quite small and the amount of rotation required to pass the projection 20 is minimal such that as the surgeon continues to rotate the screw 100 he will come to the maximum diameter as shown in FIG. 3B. At this point the resistance is the highest and the deflection is the highest of the screw head 110 and as the surgeon continues to rotate the driver as shown in FIG. 3C, the entire screw head 110 will pass at the location at the location of the maximum diameter $D_M$ and the projections 20 will reside upward along the surface curvature 112 of the side of the screw head 110 as illustrated in FIG. 3C. At this point, the surgeon simply does the final turn or turns as needed to securely anchor the screw 100 into the bone, at this point the projections 20 are now automatically in position preventing the screw head 110 from backing out. It is noted that the projections 20 are of sufficient size such that as the screw 100 is attempted to be backed out, particularly in the exemplary embodiment, it is possible to withdraw the screw 100 with a screw driver, however, the screw 100 will not under vibration or under normal movement back out on its own. As the locking feature 20 would require the screw head 110 to deflect in a direction back toward the recessed groove 30 to come back out of the receiver opening 12.

This is quite novel and provides a unique capability of the device in that as the surgeon rotates the screw driver anchoring the screw 100 to the bone, he will engage the projection 20 feel a resistance, which maximizes at the maximum diameter and as the screw 100 passes over the maximum diameter, he will feel a decrease in pressure. This is noticeable and the surgeon can feel the fact that he has now locked the screw head 110 in place. While there is no audible sound necessarily, what is occurring is an ability to feel the lock engage the screw head 110 as the surgeon is applying torque to the driver.

As shown in the bottom of the opening 12 is the seat 14, in whatever device the screw 100 is being mounted into, it is preferable that the seat 14 be a design to hold the screw head 110 in position whether it be in a polyaxial, monoaxial, dual axial or a fixed axis. There is preferably always a seat 14 upon which the screw head 110 rests upon final tightening. This feature has to be positioned in such a way that the projections 20 are sufficiently spaced above the seat 14 to allow the screw head 110 to pass the maximum diameter and to be held tightly therein in a fully seated position. This can occur typically by creating a slight contour on the projections as illustrated in FIG. 3C. As shown, the nubs or projections 20 have a sloped upper and lower surface extending into the wall 11.

Figure 5A:
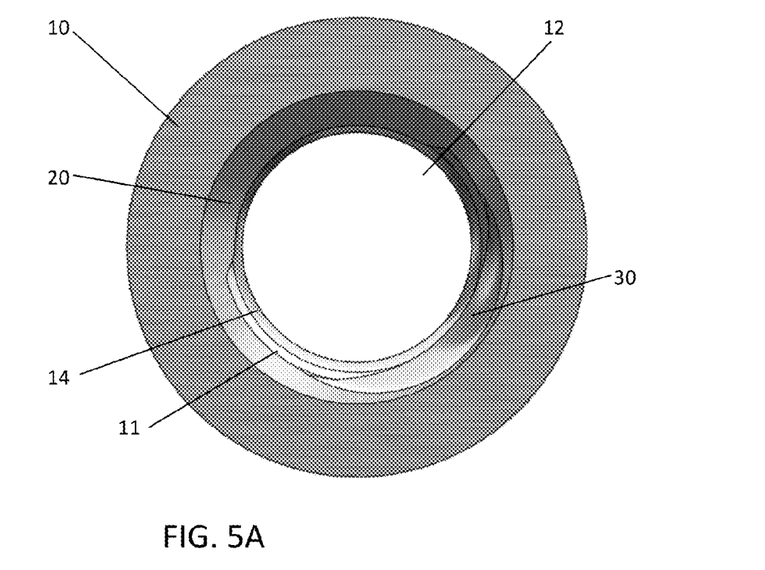
FIG. 5A is a top view of the self-locking feature as an arcuate projection in the exemplary receiving opening without a screw installed.
Figure 5B:
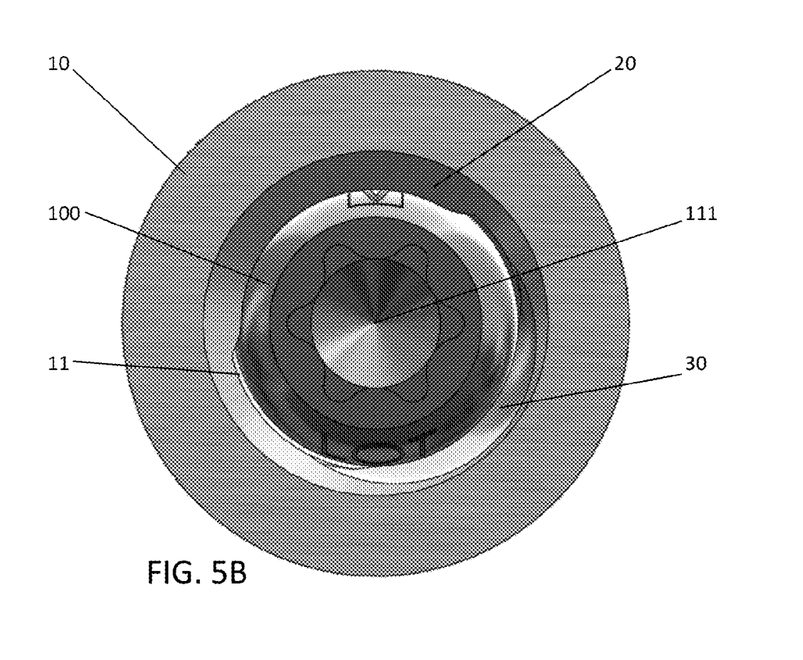
FIG. 5B is a top view of the self-locking feature as an arcuate projection in the exemplary receiving opening of FIG. 5A with a screw installed.

While the preferred embodiment shows the use of two nubs or projections 20, it is important to understand that these nubs 20 could be created as an arcuate segment as a single projection 20, as shown in FIGS. 5A and 5B. However, in such a case, the single projection 20 should not extend beyond 120 degree typically so that the directional effect can be achieved. It is noted that two nubs 20 provides a minimal amount of locking impedance, however, this minimal amount is sufficient to secure the screw head 110 and to provide a minimal resistance. An advantage of the present invention is that the dimensions on current polyaxial or bone screws 100 are such that they vary within a few thousandths of an inch. This few thousandths variation is easily accommodated by the fact that the projections 20 can extend out a reasonable amount further than the minimum diameter tolerance to the screw head 110 such that it will allow the deflection to occur and furthermore the projections 20 are designed so that the maximum diameter produced polyaxial bone screw head can accommodated as well because the recessed groove 30 is designed sufficiently deep to allow variations in sizes of screw heads. All the tolerance variations are taken out by the ability to create a deflection in the recessed groove 30. Alternative to a recessed groove 30 is to provide the entire opening 12 of a sufficiently large diameter to accommodate this and to take out the tolerances below the maximum diameter by the seat 14. While this can occur, it is believed preferable that the walls 11 of the receiving opening 12 should be sized sufficiently to provide a rather close fit between the screw head 110 and the receiver opening 12. When close fit is desirable, it is therefore preferred to achieve deflection accommodation by using the recessed groove 30 positioned diametrically opposite the projection 20. As mentioned, the projection 20 can be a single projection extending in an arcuate circle as shown in FIG. 5. This means that the projection 20 would encircle approximately 120 degrees of the screw head 110. This provides a reasonable amount of engagement. However, it is noted that entire distance between the two nubs 20 can be cut out as illustrated earlier meaning the locking feature 20 would only make contact at two locations. Again though, these two nub locations are spread out approximately 120 degrees around the circumference of the screw head 110.

As shown, the exemplary receiver 10 is shown simply as a basic exemplary mock-up type structure. It is understood that this opening 12 can be put in any type of implant receiver type device such as a tulip receiver, tower receiver, for receiving a polyaxial screw, a bone anchor plate, cervical or lumbar plate for having multiple holes or openings 12, each of which could have this projection 20, or in a spinal implant device having an opening 12 for bone screws 100. In all of these receiver devices 10, the same opening 12 with nubs or a projection 20 are contemplated. In any device currently manufactured that employs a locking feature it is believed that the present invention can replace any separate locking feature in a rather simple and positive manner by the use of combination of a deflecting projection 20 on one side with an accompanying recess 30 on the other side to allow the screw head 110 to deflect upon insertion.

As shown, during testing with cervical bone screws, variations in sizes of the projections 20 were accommodated and the forces range from very high initially to very low. It was determined that projections providing less than 2 lbs of resistance may be insufficient to prevent the screw head 110 from moving out. Accordingly a half pound resistance may or may not be sufficient. However, between 2 lbs and 6 lbs it was found that the screw heads 110 would not back out. Accordingly, as a design safety margin, it is believed important that the screw heads 110 of cervical bone screws be positioned with a resistance force of 2-6 lbs, preferably 4 lbs. Interestingly, the design is so accommodating and because of the deflection capability upon insertion it has been found that the projections 20 can easily provide a consistent 4 lb insertion if so desired, regardless of the tolerances of the screw head 110 regardless of the variation in current manufacturing practices within the bone screws 100 which are a titanium or stainless steel product typically.

It was further found that if the cervical bone screw locking feature exceeded 10 lbs force, it made it rather difficult for the surgeon to penetrate the projections 20 in such a fashion that, once penetrated, he might over torque the underlying bone. It is therefore important that when using the present invention that the forces stay within the preferred range of 2-6 lbs so that the surgeon can feel comfortable on the insertion of the screw 100 without jeopardizing having either too difficult to insert or too easy to insert tolerances. Other types of bone screws may have a different range of optimum dimensions and deflection to achieve the appropriate forces. These forces may be selected to be higher or lower than the example given.

A key advantage of the invention, as illustrated, is that it can be provided without any additional parts. A simple machining operation creates the projection 20 in the device without any added material or components. This is unlike any locking feature that is provided as a separate component to the implant device. Another advantage is the screw 100, once inserted, can just as easily be removed by use of the screw driver simply unscrewing the screw fastener 100. The screw head 110 will deflect again as it withdraws past the projection 20 or nubs 20 as it disengages the bone. No special tools or unlocking devices are required.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A self-locking screw assembly comprising:
a screw receiver opening for receiving a polyaxial screw, a bottom of the opening having a seat to hold a screw head;
a polyaxial screw with a screw head having a spherical contoured surface increasing from a shank to a maximum diameter $D_M$; and
a self-locking feature formed in a wall surface of the screw receiver opening for automatically preventing the backing out of the screw, wherein the self-locking feature is one or more nubs or projections formed into the surface wall in an eccentric orientation on one half of the receiver opening extending 120 degrees or less and spaced above the seat to allow the screw head to pass at the maximum diameter, and upon threading the screw, the one or more projections push against the screw head in a common direction away from the one or more nubs or projections as the screw head initially contacts the one or more nubs or projections, causing the screw head to deflect in the common direction until threaded past all of the one or more nubs or projections clearing the maximum diameter, the screw being tightened against the seat, and when the screw is tightened against the seat, the one or more nubs or projections reside along the surface curvature of the screw head.

2. The self-locking screw assembly of claim 1 wherein the one or more nubs or projections is either one projection extending 120 degrees or less arcuately around the inner wall surface or two nubs spaced 120 degrees or less apart around the inner wall.

3. The self-locking screw assembly of claim 2 wherein the one projection or two nubs extend outwardly from the inner surface of the wall a distance P and the receiver opening has a diameter sufficiently large to allow the screw head to deflect past the one projection or two nubs, the one projection or two nubs having a sloped upper and lower surface creating a slight contour extending into the wall, wherein the tightened screw can be removed by simply unscrewing the screw.

4. The self-locking screw assembly of claim 1 wherein the self-locking feature allows the screw to pass at less than 10 inch pounds torque.

5. The self-locking screw assembly of claim 4 wherein the self-locking feature allows the screw to pass at between 2 and 6 inch pounds torque.

6. The self-locking screw assembly of claim 5 wherein the screw passes at 4 inch pounds torque.

7. The self-locking screw assembly of claim 1 is one of the following selected from a group of a bone plate, a bone implant, a receiver tower, a receiver tulip, cervical or lumbar plate or any other bone anchoring device having an opening with the self-locking feature to prevent the backing out of the screw.

8. A self-locking screw assembly comprising:
a screw receiver opening for receiving a polyaxial screw, a bottom of the opening having a seat to hold a screw head;
a polyaxial screw with a screw head having a spherical contoured surface increasing from a shank to a maximum diameter $D_M$; and
a self-locking feature formed in a wall surface of the screw receiver opening for automatically preventing the backing out of the screw, wherein the self-locking feature is one or more nubs or projections formed into the surface wall in an eccentric orientation on one half of the receiver opening extending 120 degrees or less and spaced above the seat to allow the screw head to pass at the maximum diameter, and upon threading the screw, the one or more projections push against the screw head in a common direction away from the one or more nubs or projections as the screw head initially contacts the one or more nubs or projections, causing the screw head to deflect in the common direction until threaded past all of the one or more nubs or projections clearing the maximum diameter, wherein the inner wall of the receiver opening is sized for a close fit between the screw head and the receiver opening, wherein the inner wall has a recessed groove cut into the wall to provide a void depression or concavity diametrically opposite the projections or nubs to receive a portion of a deflected screw head as the maximum diameter of the screw head deflects and is driven past the projections or nubs, the screw being tightened against the seat, and when the screw is tightened against the seat, the one or more nubs or projections reside along the surface curvature of the screw head.

9. The self-locking screw assembly of claim 8 wherein the one or more nubs or projections is either one projection extending 120 degrees or less arcuately around the inner wall surface or two nubs spaced 120 degrees or less apart around the inner wall.

10. The self-locking screw assembly of claim 9 wherein the one projection or two nubs extend outwardly from the inner surface of the wall a distance P and the receiver opening has a diameter sufficiently large to allow the screw head to deflect past the one projection or two nubs, the one projection or two nubs having a sloped upper and lower surface creating a slight contour extending into the wall, wherein the tightened screw can be removed by simply unscrewing the screw.

11. The self-locking screw assembly of claim 8 wherein the self-locking feature allows the screw to pass at less than 10 inch pounds torque.

12. The self-locking screw assembly of claim 11 wherein the self-locking feature allows the screw to pass at between 2 and 6 inch pounds torque.

13. The self-locking screw assembly of claim 12 wherein the screw passes at 4 inch pounds torque.

14. The self-locking screw assembly of claim 8 is one of the following selected from a group of a bone plate, a bone implant, a receiver tower, a receiver tulip, cervical or lumbar plate or any other bone anchoring device having an opening with the self-locking feature to prevent the backing out of the screw.

* * * * *